United States Patent [19]

McNaughton

[11] Patent Number: 5,024,660

[45] Date of Patent: Jun. 18, 1991

[54] SYRINGE SHIELD

[76] Inventor: R. David McNaughton, 95 Dobler Ave., Alberta, Canada

[21] Appl. No.: 406,276

[22] Filed: Sep. 12, 1989

Related U.S. Application Data

[63] Continuation-in-part of Ser. No. 130,277, Dec. 8, 1987, Pat. No. 4,874,383.

[30] Foreign Application Priority Data

Mar. 17, 1987 [CA] Canada ................................. 532233

[51] Int. Cl.$^5$ ............................................ A61M 5/00
[52] U.S. Cl. ................................. 604/110; 604/198; 604/263
[58] Field of Search ............... 604/198, 192, 187, 263, 604/110

[56] References Cited

U.S. PATENT DOCUMENTS

| | | | |
|---|---|---|---|
| 4,743,23 | 5/1988 | Schneider | 604/198 X |
| 2,571,653 | 10/1951 | Bastien | |
| 2,845,065 | 7/1958 | Gabriel | |
| 3,073,306 | 1/1963 | Linder | |
| 3,783,998 | 1/1974 | Brush et al. | |
| 4,356,822 | 11/1982 | Winstead-Hall | |
| 4,425,120 | 1/1984 | Sampson et al. | |
| 4,573,976 | 3/1986 | Sampson et al. | |
| 4,631,057 | 12/1986 | Mitchell | |
| 4,666,435 | 5/1987 | Braginetz | 604/198 |
| 4,702,738 | 10/1987 | Spencer | 604/198 |
| 4,723,943 | 2/1988 | Spencer | |

FOREIGN PATENT DOCUMENTS

| | | |
|---|---|---|
| 593226 | 2/1960 | Canada . |
| 689751 | 6/1964 | Canada . |
| 912389 | 10/1972 | Canada . |
| 953594 | 8/1974 | Canada . |
| 1001032 | 12/1976 | Canada . |
| 1164753 | 4/1984 | Canada . |

Primary Examiner—John D. Yasko
Attorney, Agent, or Firm—Hoffman, Wasson & Gitler

[57] ABSTRACT

Disclosed are hypodermic syringes having special safety features for preventing the user from inadvertently pricking himself with the needle. In the preferred embodiment the barrel of, for example, a syringe is provided with a sleeve that can be drawn out over the needle and firmly locked into position to prevent accidental contact of the user with the needle.

21 Claims, 2 Drawing Sheets

SYRINGE SHIELD

This application is a continuation-in-part of applicant's co-pending U.S. patent application Ser. No. 130,277 now U.S. Pat. No. 4,874,383.

FIELD OF THE INVENTION

This invention relates to hypodermic needles, and especially a syringe assembly, and specifically to such assembly that is safe to use in a medical environment.

DESCRIPTION OF THE PRIOR ART

Typical means for ensuring the sterility of a hypodermic needle prior to use, and for the protection of a handler subsequent to use, include the familiar cap that seats on a collar surrounding the needle. However, these caps do not reliably protect persons handling the syringe after use. There have been numerous instances of injuries and consequent infection caused by users trying to slide a cap back over a needle, and in doing so puncturing their own skins. While in many instances little harm results from such injuries, with the advent of auto-immune disease syndrome (AIDS) medical persons have viewed with greater alarm the ease with which a potentially contaminated needle can puncture the skin of anyone handling the syringe subsequent to the administration of an injection to or the withdrawal of blood from a patient who may have a highly communicable disease.

The typical modern syringe is a disposable item having a plunger, barrel and needle with a protective cap over the needle. Many attempts have been made to improve on the conventional needle protection means described above, and perhaps the most relevant known to applicant is disclosed in U.S. Pat. No. 4,356,822 granted on Nov. 2, 1982 (Winstead-Hall). The syringe disclosed in the patent has the usual barrel, plunger and needle, however, an additional sleeve is slidable over the barrel. The primary purpose of the sleeve is to provide a means for determining precisely the depth of penetration of the needle 6, in FIG. 1 of the patent, into human tissue. The patentee clearly had in mind safety, i.e., minimizing undesired puncture wounds by the users. However, the patent does not address the problem of the security of the sleeve when it is positioned over the needle subsequent to the use of the syringe.

There remains a need for a disposable syringe assembly having a safety cover which, once locked in position, cannot, without the use of considerable force, be removed from its locked position.

SUMMARY OF THE INVENTION

The present invention overcomes the disadvantages of the prior art identified above by providing locking means between an auxiliary sleeve and the barrel of the syringe for securely locking the sleeve in a fully extended position in which the needle is fully covered to prevent injury to a user by the needle. More specifically, the invention provides a syringe comprising: a barrel having an hypodermic needle mounted on one end thereof, a piston mounted for movement longitudinally within the barrel and connected to a handle that projects from the opposite end of said barrel; wherein said barrel is tubular and at least partially transparent in a portion that extends over the major part of its length; a tubular sleeve dimensioned to fit over the barrel, and guided to slide axially thereon between an extended position wherein it projects from said one end of the barrel beyond the tip of said needle and a retracted position wherein it coaxially surrounds said barrel and exposes said needle for use, said sleeve having a length that corresponds to that of said barrel and comprising a tubular wall that is at least partially transparent such that in said retracted position it affords unimpeded visibility of substantially the entire length of said transparent portion of said barrel; retaining means to secure said sleeve when in the retracted position against axial movement relative to said barrel; and locking means for securely and non-releasably locking the sleeve in said extended position, in which position the needle is fully covered to prevent injury to a user by the needle.

The retaining means retains the sleeve over the barrel to prevent inadvertent displacement of the sleeve so that the clear central portion of the sleeve provides unimpeded viewing of the barrel up to and during the time of use. After use the sleeve is moved to its extended position and the locking means are engaged to securely lock the sleeve in this position.

Preferably, a screw-on cap is provided to place over the end of the sleeve once it has been fully extended and locked in position.

The invention provides a cheaply constructed, disposable syringe that materially improves safety in that a deliberate and almost self-destructive act would be required before the needle could contaminate the user.

BRIEF DESCRIPTION OF THE DRAWINGS

In the drawings, which illustrate embodiments of the invention.

DESCRIPTION OF THE PREFERRED EMBODIMENT

Figure 1:
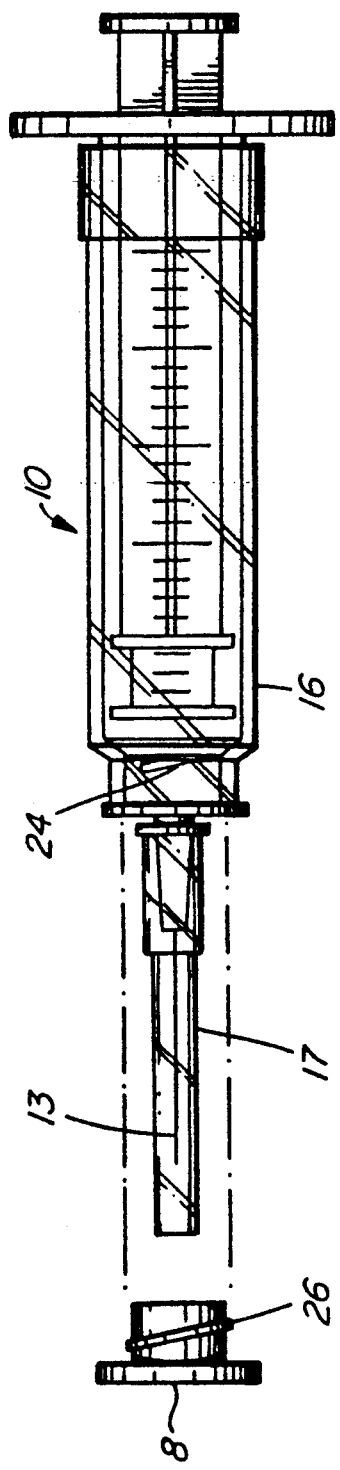
FIG. 1 is a side elevation of a syringe according to the invention.

In the drawings, 10 is a syringe having a transparent cylindrical barrel 11, a plunger 12 bearing a piston 15, and a needle 13. Indicia 14 on the barrel 11 indicate, by reference to the end of the piston 15, the amount of fluid drawn into the syringe.

A tubular cylindrical sleeve 16 is dimensioned to fit closely over the barrel 11 so that in its initial position it covers the barrel 11 entirely, allowing the needle 13 to project beyond the end of the sleeve, that is, to the left in FIG. 1. The sleeve 16 is transparent and is of substantially uniform thickness over the major portion of its length so that when the sleeve 16 is in its initial, retracted position as shown in FIG. 1, the barrel 11 and its contents as well as the indicia 14 are clearly visible over their entire extent. The syringe is provided, as packaged, with a standard smaller sleeve 17 of the type known in the art which, in the case of the present invention, is removed prior to use and discarded, since it need not be used again. Barrel 11 and sleeve 16 are formed from a suitable plastic material.

Figure 2:
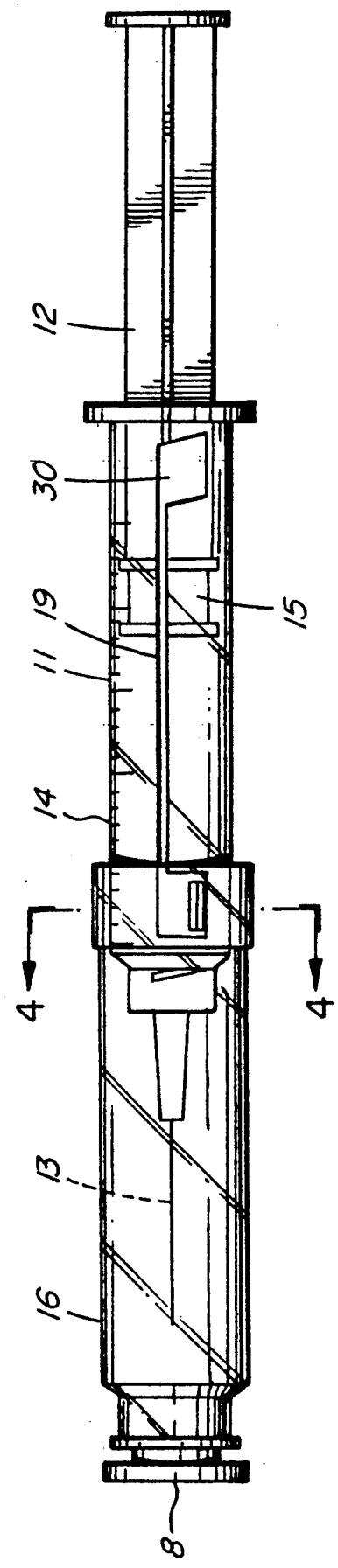
FIG. 2 is a view similar to FIG. 1 with its protective sheath extended.
Figure 3:
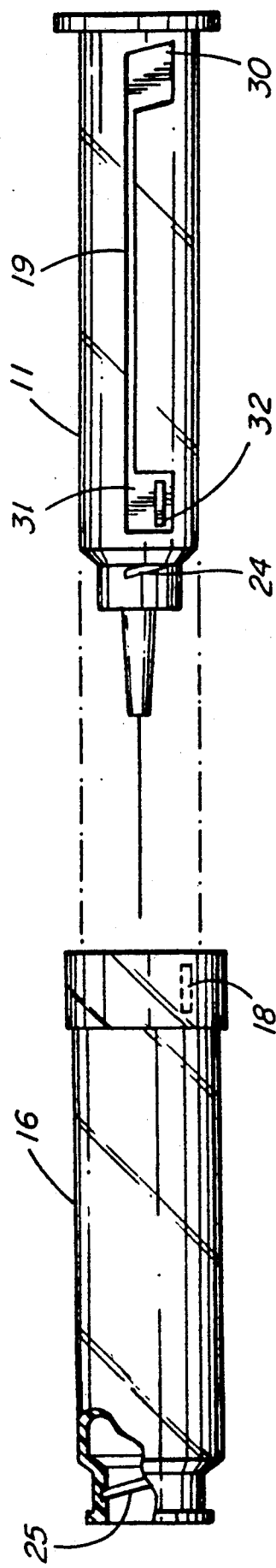
FIG. 3 is an illustration of the syringe with the sheath separated therefrom.
Figure 4:
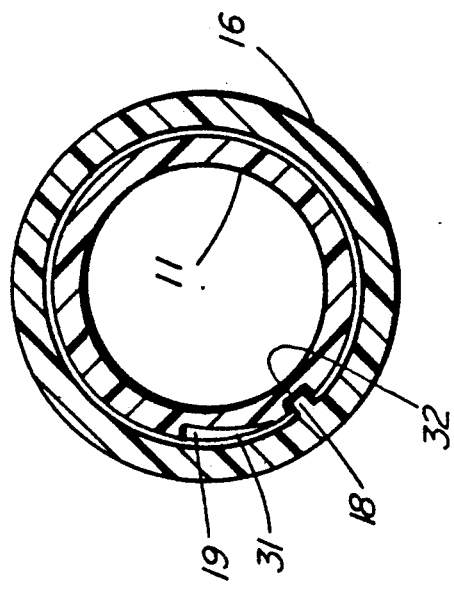
FIG. 4 is a section on the line 4—4 of FIG. 2.

The sleeve 16 is secured prior to use by the screw threads at 24 on the outside of the barrel 11, and matching screw threads 25 on the inside of the distal end of the sleeve. The screw threads 24 are formed, in a manner known in the art, such that a quarter-turn of the sleeve 16 in relation to the barrel 11 releases the sleeve 16 for axial movement along the barrel 11. In FIG. 2, the sleeve 16 is shown fully extended to a position where it entirely covers the needle 13, and it is impossible to make accidental physical contact with the needle. Preferably, a cap 8 is provided having external threads 26 matching the threads 25. The cap is packaged with the syringe 10 and used to ensure the safety of the assembly after use.

Illustrated on the outside of the barrel 11 is a formation, in the plastic material from which the barrel is formed, of a feature critical to the invention, i.e., the aforementioned secure locking means. Formed on the inside of the sleeve 16 is a protrusion 18 that extends radially inwardly a short distance corresponding to a groove 19 (FIG. 2) formed in the outside of the barrel 11. The groove 19 extends axially along the barrel, and at its right hand or inner end extends circumferentially as at 30 to permit the aforementioned quarter turn locking of the sleeve in the rest position via the threads 24,25. This lateral extension 30 of the groove 19 therefore extends over a quarter, or slightly more than a quarter, of the circumference of the barrel 11. The depth of the lateral extension 30 of groove 19 is such that the protrusion 18 will enter and form a tight fitting frictional engagement therewith. The protrusion will thus be frictionally held in the extension 30 and requires substantial force to be applied to disengage it and move it into alignment with the groove 19. This frictional engagement between the extension 30 and the protrusion 18 provides a further locking means to retain the sleeve 16 in the retracted position. At the opposite or outer end of the groove 11, a ramp 31 is formed extending in depth from its maximum at the groove 19 radially outwardly to a recess 32 corresponding in size and shape to the protrusion 18. Thus, once the sleeve has been rotated a quarter turn freeing it from the threads 24 and freeing it from the portion 30 of the groove, the sleeve can be pulled along the barrel with the protrusion 18 engaged in the groove 19 to its outermost or left hand position. Rotation of the sleeve 16 then causes the protrusion 18 to ride resiliently up the ramp 31 (this movement being accommodated by flexure of the sleeve 16 and/or the barrel 11) and drop into the recess 32, thus locking the sleeve firmly in the disposal position shown in FIG. 2. It will be appreciated that the sleeve 16 cannot be removed from the locked position without considerable force applied either torsionally or axially and as a consequence the user is protected, as are, for example, cleaning staff. The cap 8 is subsequently screwed into position in the barrel to complete the protective covering.

It will also be understood that while the invention is primarily intended for use with a syringe, other assemblies having percutaneous needles can be equipped in like manner with protective sleeves.

What I claim as my invention is:

1. A syringe comprising:
   a barrel having an hypodermic needle mounted on one end thereof, a piston mounted for movement longitudinally within the barrel and connected to a handle that projects from the opposite end of said barrel; wherein said barrel is tubular and at least partially transparent in a portion that extends over the major part of its length;
   a tubular sleeve dimensioned to fit over the barrel, and guided to slide axially thereon between an extended position wherein it projects from said one end of the barrel beyond the tip of said needle and a retracted position wherein it coaxially surrounds said barrel and exposes said needle for use, said sleeve having a length that corresponds to that of said barrel and comprising a tubular wall that is at least partially transparent such that in said retracted position it affords unimpeded visibility of substantially the entire length of said transparent portion of said barrel;
   retaining means to secure said sleeve when in the retracted position, said retaining means being effective to prevent any inadvertent axial or rotational movement of said sleeve relative to said barrel; and
   locking means for securely and non-releasably locking the sleeve in said extended position, in which position the needle is fully covered to prevent injury to a user by the needle.

2. A syringe as claimed in claim 1 wherein said sleeve has an internal projection and said locking means comprise walls that define a locking recess in said barrel into which recess said projection can be positioned by predetermined angular movement of said sleeve relative to said barrel in said extended position, said barrel including an inclined ramp that approaches said locking recess to guide and facilitate entry of said projection unto said recess.

3. A syringe as claimed in claim 1, comprising a projection on the inside of the sleeve, and guide means on the outside of the barrel to guide the sleeve for axial movement from said retracted position to said extended position, said projection in the extended position being in register with a peripherally extending inclined ramp that terminates in a recess that comprises said locking means and is dimensioned to accommodate and non-releasably retain the projection, so that by resilient deflection said projection is movable over said ramp upon rotation of said sleeve and drops into the recess to lock the sleeve in the extended position.

4. A syringe as claimed in claim 1 wherein said sleeve is of molded plastic material and the cylindrical wall thereof is of substantially constant thickness.

5. A syringe comprising:
   a barrel having an hypodermic needle mounted on one end thereof said needle including a tip portion, a piston mounted for movement longitudinally within the barrel and connected to a handle that projects from an opposite end of said barrel; wherein said barrel is tubular;
   a tubular sleeve dimensioned to fit over the barrel, and mounted to slide axially thereon between an extended position wherein at least a portion of said tubular sleeve projects from said one end of the barrel beyond the tip portion of said needle and a retracted position wherein said tubular sleeve coaxially surrounds said barrel and exposes said needle for use, said sleeve including an internal projection;
   locking means for securely locking said sleeve in said extended position in which said needle is fully covered to prevent injury to a user by said needle, said locking means comprising walls on said barrel that define a locking recess in said barrel into which locking recess said internal projection can be positioned by predetermined rotational movement of said sleeve relative to said barrel in said extended position, said barrel including a radially inclined ramp adjacent one of said walls of said locking means to guide and facilitate entry of said projection into said locking recess by said predetermined rotational movement of said sleeve relative to said barrel in said extended position; and retaining means to releasably secure said sleeve when in the retracted position against axial movement relative to said barrel.

6. A syringe as claimed in claim 5 wherein said retaining means comprises a screw-thread formed on an end portion of said sleeve and engageable with a complimentary screw-thread formed on said barrel when said sleeve is in the retracted position to retain said sleeve against inadvertent axial or rotational movement.

7. A syringe as claimed in claim 5, further comprising a guide means on the outside of the barrel to guide the sleeve for axial movement from said retracted position to said extended position, said internal projection in the extended position being in register with said extending inclined ramp terminating at said locking recess which is dimensioned to accommodate and nonreleasably retain said internal projection, whereby, said projection is resiliently deflected as said projection is moved over said ramp upon rotation of said sleeve, until said projection drops into said locking recess to lock said sleeve in the extended position.

8. A syringe as claimed in claim 7 wherein said retaining means comprises a screw-thread formed on an end portion of said sleeve and engageable with a mating screw-thread formed on said barrel when said sleeve is in the retracted position to retain said sleeve against inadvertent axial or rotational movement.

9. A syringe as claimed in claim 8 wherein the rotation of said sleeve to effect full engagement of said screw-threads amounts to approximately one quarter of a full rotation.

10. A syringe as claimed in claim 9 comprising a screw-threaded cap engageable with said screw-thread on said sleeve when the latter is in the extended condition to completely close the associated end of the sleeve.

11. A medical device comprising:
a barrel having a hypodermic needle mounted on one end thereof, said hypodermic needle including a tip portion, said barrel being of cylindrical form over a portion of its length;
a sleeve dimensioned to fit over said barrel, and mounted to be slidable between an extended position wherein said sleeve projects from said one end of said barrel beyond the tip portion of said needle and a retracted position wherein said sleeve coaxially surrounds said barrel and exposes said needle for use;
locking means for securely locking said sleeve in said extended position in which said needle is fully covered to prevent injury to a user by said needle, said locking means comprising walls that define a locking recess in said barrel into which recess said internal projection can be positioned by predetermined movement of said sleeve relative to said barrel in said extended position, said barrel including an inclined ramp that approaches said locking recess to guide and facilitate entry of said projection into said recess; and
a retaining means to releasably secure said sleeve when in said retracted position against axial movement relative to said barrel.

12. A medical device comprising:
a barrel having a hypodermic needle mounted on one end thereof, said hypodermic needle including a tip portion, said barrel being of cylindrical form over the major portion of its length;
a sleeve dimensioned to fit over said barrel, and mounted to be slidable there along, said sleeve being movable axially between an extended position wherein it projects from said one end of said barrel beyond the tip portion of said needle and a retracted position wherein it coaxially surrounds said barrel and exposes said needle for use;
a projection on the inside of said sleeve, a mating groove extending along the outside of said barrel, an inclined ramp extending transversely from said groove and terminating in a recess that comprises locking means for securely locking said sleeve in said extended position in which said needle is fully covered to prevent injury to a user by said needle, said recess being dimensioned to accommodate and retain said projection, said projection being movable along said groove as said sleeve is moved axially along said barrel until said projection registers with said ramp, further rotational movement of said sleeve causing said projection to move up said ramp and then to drop into said recess to lock said sleeve in the extended position; and
retaining means to releasably secure said sleeve when in said retracted position against axial movement relative to said barrel.

13. A medical device as claimed in claim 12 wherein said retaining means comprises a screw-thread formed on an end portion of said sleeve and engageable with a mating screw-thread formed on said barrel when said sleeve is in the retracted position to releasably secure said sleeve against axial movement, said groove having a circumferential extension to accommodate said projection during rotation of said sleeve upon engagement or disengagement of said mating screw threads.

14. A medical device as claimed in claim 13 wherein the rotation of said sleeve to effect full engagement of said screw-threads of said sleeve to effect full engagement of said screw-threads amounts to approximately one quarter of a full rotation.

15. A medical device as claimed in claim 14 further comprising a screw-threaded cap engageable with said screw-thread on said sleeve when the latter is in the extended condition to completely close the associated end of the sleeve.

16. A medical device comprising:
a tubular barrel having a hypodermic needle coaxially mounted at a distal end thereof, said hypodermic needle including a tip;
a sleeve dimensioned to fit over said barrel and mounted to be axially movable there along between an extended position wherein said needle tip is covered and a retracted position wherein said needle tip is exposed;
a projection on the inside of said sleeve, a mating groove extending axially along the outside of said barrel, an inclined ramp extending transversely from said groove and terminating in a wall projecting from said barrel, said projection being axially movable along said groove from said retracted position in response to axial movement of said sleeve along said barrel until said projection is aligned with said ramp, said projection then being rotatably movable relative to said barrel in response to rotational movement of said sleeve relative to said barrel to move said projection along said inclined ramp to a position atop said wall, continued rotational movement of said sleeve relative to said barrel causing said projection to move from atop said wall to a position behind said wall.

17. A medical device comprising:
   a barrel having a hypodermic needle mounted on a distal end thereof, said hypodermic needle including a distal tip portion;
   a sleeve dimensioned to fit over said barrel, and mounted to be slidable there along, said sleeve being axially between an extended position wherein said sleeve projects from said distal end of said barrel beyond the tip portion of said needle and a retracted position wherein said sleeve exposes the tip portion of said needle for use;
   locking means for securely locking said sleeve in said extended position;
   securing means comprising a screw-thread formed on said sleeve near a distal end thereof and engageable with a mating screw-thread formed on said barrel near said distal end of said barrel when said sleeve is in the retracted position to releasably secure said sleeve against axial movement.

18. A medical device according to claim 17 further including a screw-threaded cap engageable with said screw-thread on said sleeve when the latter is in the extended position to completely close the distal end of said sleeve.

19. A medical device as claimed in claim 17 wherein the rotation of said sleeve to effect full engagement of said screw-threads amounts to approximately one quarter of a full rotation.

20. A medical device as claimed in claim 18 wherein said screw-threaded cap includes means for preventing puncturing of said cap by said needle.

21. A syringe comprising:
   a barrel having an hypodermic needle mounted on one end thereof said needle that projects from an opposite end of said barrel; wherein said barrel is tubular;
   a tubular sleeve dimensioned to fit over the barrel, and mounted to slide axially thereon between an extended position wherein at least a portion of said tubular sleeve projects from said one end of the barrel beyond the tip portion of said needle and a retracted position wherein said tubular sleeve coaxially surrounds said barrel and exposes said needle for use, said sleeve including an internal projection;
   locking means for securely locking said sleeve in said extended position in which said needle is fully covered to prevent injury to a user by said needle, said locking means comprising walls on said barrel that define a locking recess in said barrel into which locking recess said internal projection can be positioned by predetermined movement of said sleeve relative to said barrel in said extended position, said barrel including an inclined ramp adjacent one of said walls of said locking means to guide and facilitate entry of said projection into said locking recess by said predetermined movement of said sleeve relative to said barrel in said extended position; and
   retaining means to releasably secure said sleeve when in the retracted position against axial movement relative to said barrel.

* * * * *